(12) United States Patent
Schulman

(10) Patent No.: US 7,979,140 B2
(45) Date of Patent: Jul. 12, 2011

(54) SEGMENTED ELECTRODE

(75) Inventor: Joseph H. Schulman, Santa Clarita, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 1127 days.

(21) Appl. No.: 11/637,387

(22) Filed: Dec. 12, 2006

(65) Prior Publication Data

US 2008/0139913 A1    Jun. 12, 2008

(51) Int. Cl.
*A61N 1/00* (2006.01)
(52) U.S. Cl. .................................................. 607/116
(58) Field of Classification Search .............. 600/390, 600/114; 606/41; 607/118, 119, 116, 3, 607/48, 114, 9
See application file for complete search history.

(56) References Cited

U.S. PATENT DOCUMENTS

| | | | |
|---|---|---|---|
| 5,324,323 A * | 6/1994 | Bui | 607/119 |
| 5,405,373 A | 4/1995 | Peterson et al. | |
| 5,697,536 A * | 12/1997 | Eggers et al. | 604/114 |
| 5,871,529 A | 2/1999 | Bartig et al. | |
| 6,473,653 B1 * | 10/2002 | Schallhorn et al. | 607/116 |
| 6,529,777 B1 | 3/2003 | Holmstrom et al. | |
| 2005/0131467 A1 * | 6/2005 | Boveja | 607/9 |
| 2005/0246004 A1 * | 11/2005 | Cameron et al. | 607/116 |
| 2006/0095105 A1 * | 5/2006 | Jog et al. | 607/116 |
| 2007/0187238 A1 * | 8/2007 | Whalen et al. | 204/400 |

* cited by examiner

*Primary Examiner* — George Manuel
*Assistant Examiner* — Robert N Wieland
(74) *Attorney, Agent, or Firm* — Malcolm J. Romano

(57) ABSTRACT

An electrode having a plurality of electrically conductive segments, each segment being electrically isolated from adjacent segments. The segments are adapted to control living tissue, typically a neuromuscular pathway for delivery of stimulation signals to a desired pathway. The segments may be selectively chosen for the delivery of the stimulation signals, so as to avoid delivery of stimulation signals to tissue in contact with segments not chosen.

10 Claims, 4 Drawing Sheets

SEGMENTED ELECTRODE

DETAILED DESCRIPTION

An embodiment of the present invention is directed to an electrode mounted at one end of an electrically non-conductive support structure. The support structure may be of a very small diameter and length and formed of a biocompatible material suitable for implant beneath a patient's skin. The electrode may be configured to deliver nerve or muscle stimulation signals at desired and precise locations on desired nerves or muscles. The stimulation is normally to cause a desired reaction in selected body tissue, by means of stimulation to a neuromuscular pathway. Examples of desired reactions are to: exercise weak muscles, moderate sleep apnea, control urinary incontinence, stimulate organs to carry out body functions and the like. Under such conditions, embodiments of the electrode described herein are used typically in implanted microstimulators of the type described in U.S. Pat. No. 6,185,452 which is incorporated herein in its entirety by reference.

Figure 1:
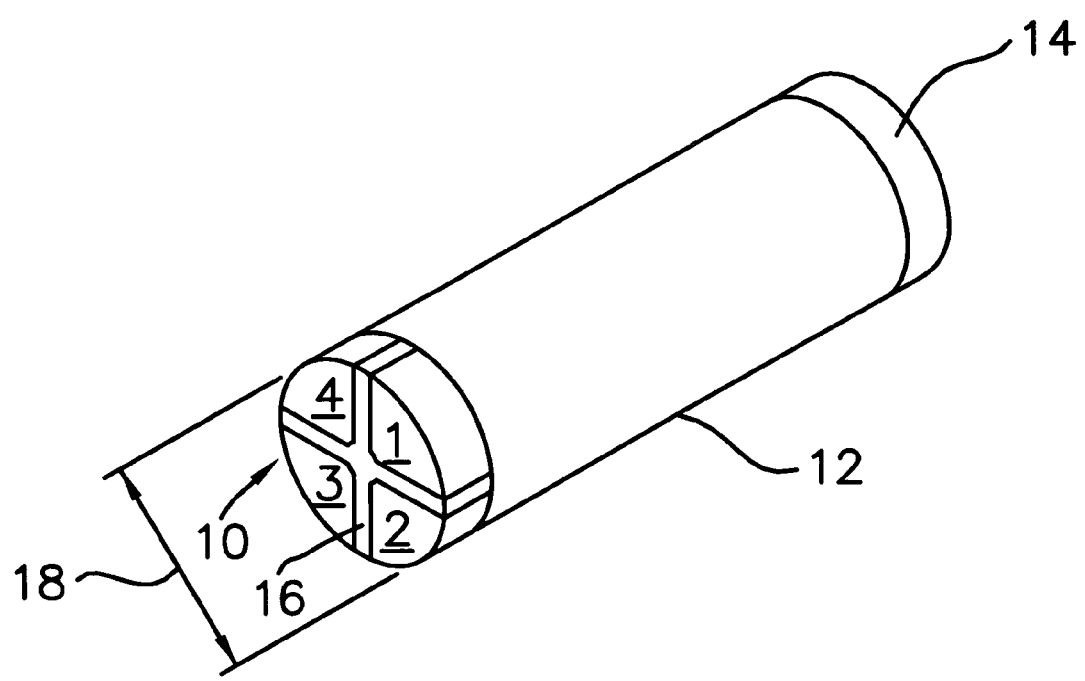
FIG. 1 is a perspective view of a segmented electrode mounted on a support structure.

FIG. 1 shows a simplified perspective view of a device that includes an electrode 10 mounted at one end of a support 12. For purposes of use in an implantable device, the support structure 12 may be a cylindrical tube formed of a biocompatible ceramic material, which is impervious to body fluids, such as, zirconia, partially stabilized zirconia, zirconia containing phase stabilization admixtures of calcia, magnesia, ceria or yttria, tetragonal zirconia polycrystalline ceramic and alumina. Biocompatible materials are those materials used in direct contact with body tissue without causing adverse effects. Preferably, the electrode 10 may be formed of platinum, iridium or platinum-iridium, which may be readily brazed to the support structure 12, (hereinafter "tube 12"). The electrode 10 may be thought of as a source of stimulation signals and electrode 14 positioned at the opposite end of tube 12, may be thought of as the stimulation signal return electrode.

Electrode 10 in FIG. 1 is shown to be divided into four individual segments, identified as 1, 2, 3 and 4. It should be understood, however, that the electrode may be divided in fewer than or more than, four segments depending upon use and design requirements, without departing from the spirit of the invention. Four segments are used purely for illustrative purposes. The segments are shown of equal dimension and size, however these characteristics are also modifiable, depending upon use and design requirements. Each of the segments 1, 2, 3 and 4 are electrically isolated from each other by means of an electrical insulating material 16, disposed between the segments. The electrical insulating material 16 may comprise a ceramic such as used for tube 12 or silicone or other biocompatible electrically insulating materials known in the art.

Figure 2:
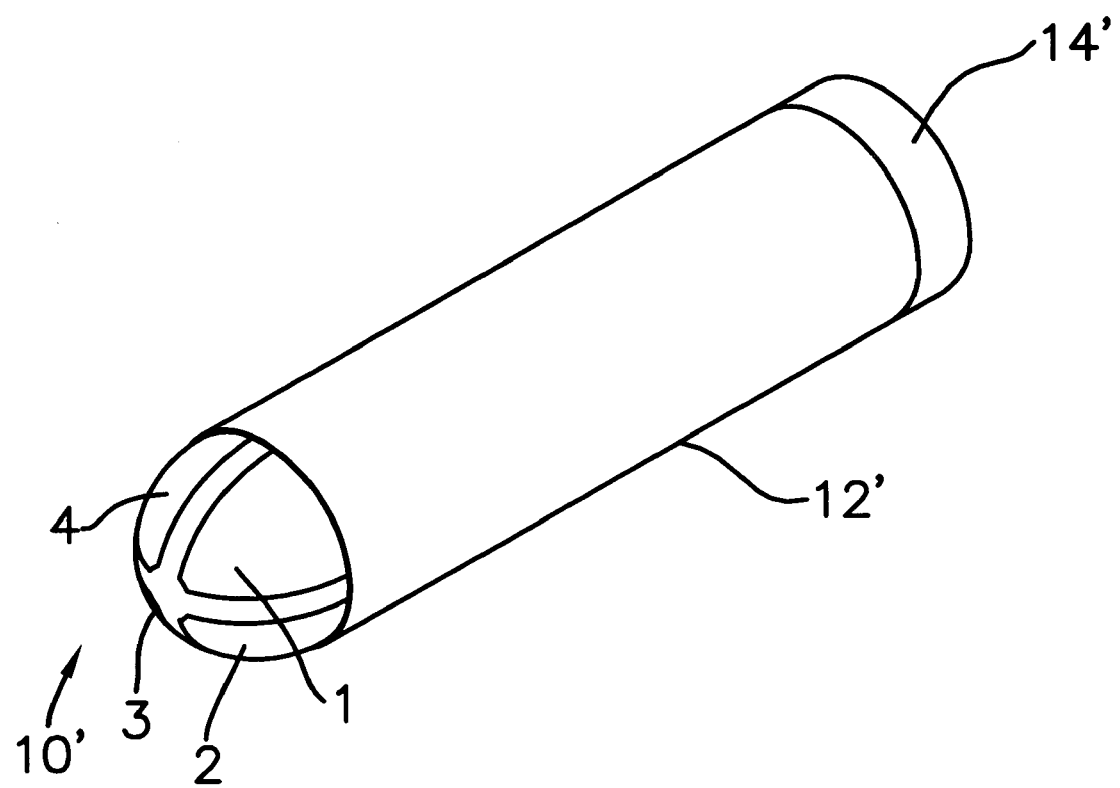
FIG. 2 is an alternate embodiment of the electrode of FIG. 1.

For the embodiment of FIG. 1, it is to be noted for the case of an electrical support structure, in the form of a cylindrical tube 12, the electrode 10 similarly may be cylindrical in form and having a circular cross section with an outer diameter 18 essentially equal to the diameter of tube 12. In such instance, the electrode 10 and tube 12 are coaxially arranged, such that there is a smooth continuous surface contour at the point of transition from the tube 12 to the electrode 10. Other shapes for the electrode 10 mounted on the tube 12 are also contemplated by the present invention. For example, as shown in FIG. 2, the electrode 10' may be dome shaped with a base having a circular cross-section and a diameter equal to that of the tube 12'. The stimulation signal return is provided by return electrode 14'. The segments may also take on the shape of a droplet (not shown) adapted for contact with tissue, in particular and demanding positions.

Figure 3:
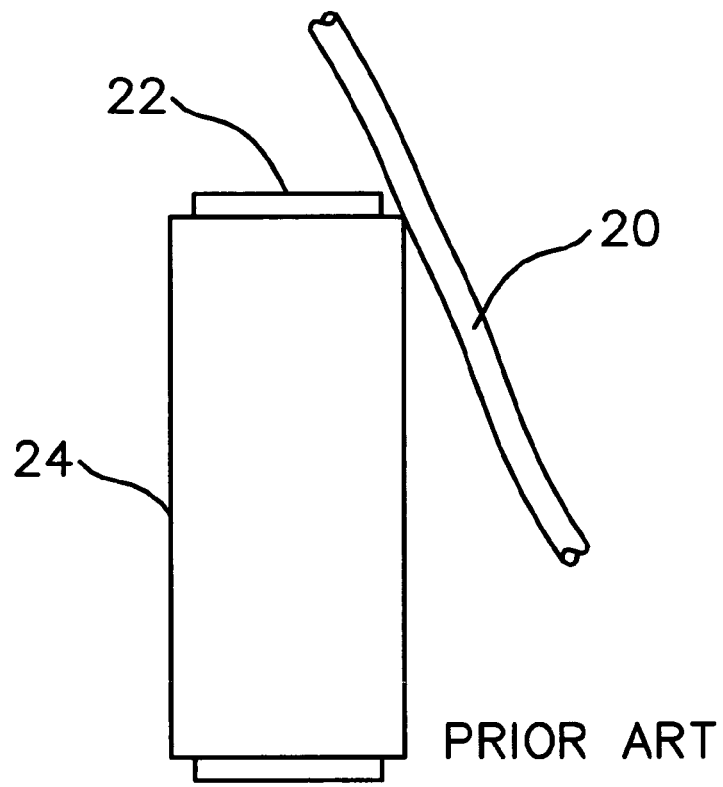
FIG. 3 is a schematic of a prior art electrode mounted on a support surface in contact with a neuromuscular pathway.

As distinct from the electrodes of the prior art shown in FIG. 3, wherein the electrode 22 is of a smaller diameter than the supporting structure 24 with the defect that notwithstanding the contact of the structure 24 with a neuromuscular pathway 20, the electrode 22 may nevertheless not contact the pathway 20 so that stimulation under such conditions may fail to occur. The electrode 10 as shown in FIG. 1, substantially reduces and even eliminates the potential of such stimulation failure since the electrode 10 extends beyond the tube 12 at the same outside diameter thereof, ensuring contact of the electrode 10 with the desired location on a neuromuscular pathway.

Figure 4:
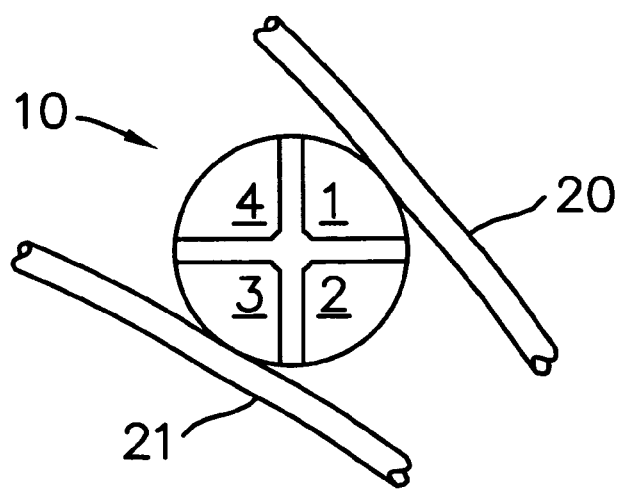
FIG. 4 is a perspective view of the segmented electrode in contact with two neuromuscular pathways.

Furthermore and with reference to FIG. 4, the electrode 10 may be positioned such that selected segments contact different pathways, such as, 20 and 21, for example. In such instance, a stimulation signal to segment 1 would affect only pathway 20, whereas a stimulation signal to segment 3 would affect only pathway 21 and so on. Accordingly, stimulation signals may be applied simultaneously to get concurrent reactions from both pathways 20 and 21, or the stimulation signals may be applied separated in time, so that a stepwise stimulation protocol may be undertaken. Otherwise, utilizing an unsegmented electrode may cause unintended stimulation of non-selected pathways during desired stimulation of selected pathways.

Another advantage of the segmented design of an embodiment of the present invention is the potential reduction of power requirements for stimulation purposes. If only one electrode segment is being utilized, then use of the other segments may not be required, thus eliminating the power delivery requirement to such other segments resulting in an overall reduction of power usage leading to extended battery life, especially with implantable devices having rechargeable internal batteries.

Figure 5:
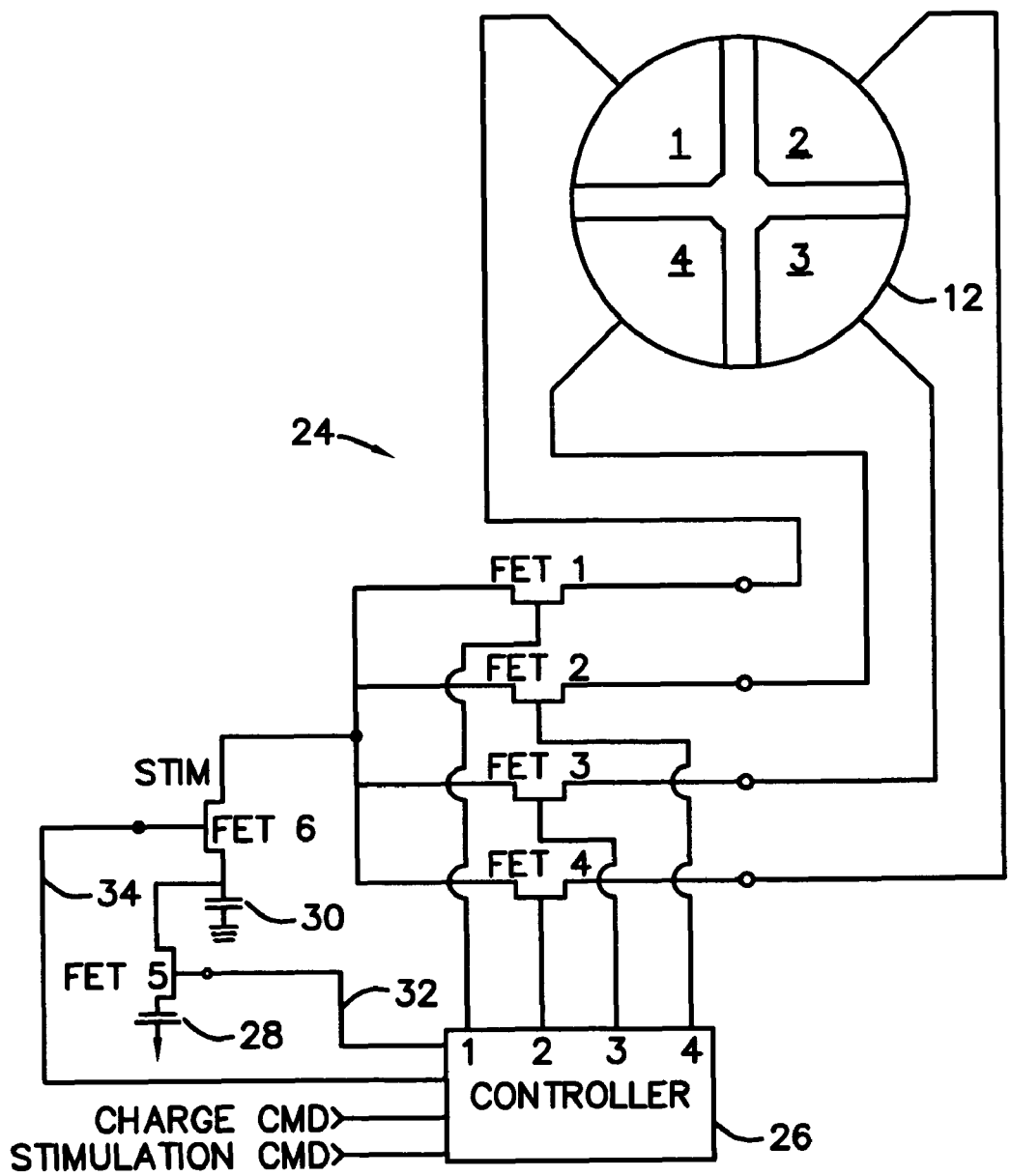
FIG. 5 is a schematic drawing of a segmented electrode coupled to a source of stimulation signals under the control of a controller.

An example electrode drive 24 circuit is shown in the schematic diagram of FIG. 5. Each electrode segment 10 is electrically coupled to controller 26 through respective switches, in this case, field effect transistors FET 1, FET 2, FET 3 and FET 4. The electrical connections between each segment and their respective switches are not shown. It is assumed that tube 12 is hollow and contains the electrical components required to provide the stimulation signals to the electrode 10, as for example, as described in U.S. Pat. No. 6,185,452. Other switch techniques and devices known in the art are also contemplated by the present invention.

The controller 26 is also coupled to charging control switch FET 5, which provides a controlled charging path from a charging battery 28 to a charge delivery capacitor 30. Further, the controller 26 is coupled to stimulation switch FET 6, which provides a stimulation signal path from capacitor 30 to the switches FET 1 through FET 4. The controller 26 may be in wireless communication with an external command and control device such as described in U.S. Pat. No. 6,185,452, that provides control signals for the commencement of the charging of capacitor 30 and delivery of stimulation signals to one or more of the elements of electrode 10, and for the timing and sequencing of such stimulation signal delivery.

In practice, controller 26 will cause FET 5 to be conductive by application of an activation signal on conductor 32 so as to charge capacitor 30 by means of battery 28. With capacitor 30 in a charged state, controller 26 will cause one or more of the desired switches selected from FET 1 through FET 4 to be conductive, depending, of course, on the corresponding electrode 10 segments selected to receive stimulation signals. Subsequently, controller 26 causes switch FET 6 to become conductive by application of an activation signal on conductor 34, providing an electrical pathway for delivery of charge (stimulation signal) on capacitor 30 to the desired electrode segments through the corresponding switches selected from FET 1 through FET 4. Sequencing the charging of capacitor 30 and delivery of the stimulation signals commences upon receipt of a CHARGE COMMAND signal and a STIMULATION COMMAND signal, respectively, typically in a wireless manner from the external command and control device.

From the foregoing it is appreciated that the electrode comprises a plurality of segments which are programmable in that any one or any combination of segments may be utilized or programmed to deliver stimulation signals to a site with which the individual segments are in contact. Furthermore, the programming of the individual segments may be changed as desired, by the controller as conditions and stimulation protocols are modified.

Thus, an electrode for electrically stimulating selected body tissue is provided. One skilled in the art will appreciate that the present invention can be practiced by other than the described embodiments, which are presented for purposes of illustration only.

The invention claimed is:

1. An electrode assembly adapted to apply stimulation signals to a neuromuscular pathway, the electrode assembly comprising a support structure having an end and an electrode mounted on such end, said support structure comprising a cylindrical tube having an outside diameter, the electrode being cylindrically shaped having an outside diameter equal to that of the support structure and being coaxial therewith, the electrode comprising a plurality of adjacent electrically conductive segments disposed around and collectively forming such end, each segment being electrically isolated from every other segment, each segment adapted for contact with a selected neuromuscular pathway, each segment configured for coupling to a source of stimulation signals so that stimulation signals are deliverable to a selected neuromuscular pathway through one or more of the segments.

2. The electrode assembly of claim 1, wherein the electrode is formed of a material selected from the group consisting of platinum, iridium and platinum-iridium.

3. The electrode assembly of claim 1, wherein an electrically non-conductive material is disposed between adjacent segments, each segment thereby being electrically isolated from every other segment.

4. The electrode assembly of claim 3, wherein the electrically non-conductive material is selected from the group consisting of: zirconia, partially stabilized zirconia, zirconia containing phase stabilization admixtures of calcia, magnesia, ceria or yttria, tetragonal zirconia polycrystalline ceramic and alumina.

5. An electrode assembly system comprising:
a support structure having an end and an electrode mounted on such end, said support structure comprising a cylindrical tube having an outside diameter, the electrode being cylindrically shaped having an outside diameter equal to that of the support structure and being coaxial therewith, said electrode adapted to apply stimulation signals to a neuromuscular pathway, the electrode comprising a plurality of electrically conductive segments collectively forming such end, each segment being electrically isolated from every other segment, each segment adapted for contact with a selected neuromuscular pathway, each segment configured for coupling to a source of stimulation signals so that stimulation signals are deliverable to a selected neuromuscular pathway through one or more of the segments;
a source of stimulation signals; and
a controller coupled between the source of stimulation signals and the electrode segments, the controller adapted to selectively interconnect the source of stimulation signals to selected ones of the plurality of electrode segments.

6. The electrode assembly system of claim 5, further comprising a plurality of segment switches, each switch coupled between the source of stimulation signals and a respective one of the plurality of segments, each switch being selectively rendered conductive by said controller for selectively interconnecting the source of stimulation signals to a respective segment.

7. The electrode assembly system of claim 6, wherein the source of stimulation signals comprises a capacitor chargeable from an energy source, the controller adapted to control the charging of the capacitor by the energy source.

8. The electrode assembly system of claim 7, wherein the source of stimulation signals further comprises a stimulation switch coupled between the capacitor and the plurality of segment switches, said stimulation switch being rendered conductive by the controller whereupon the source of stimulation signals is selectively coupled to one or more of the segments.

9. The electrode assembly system of claim 5 wherein the electrode may be programmed to deliver stimulation signals to said body tissue through one or more programmed segments.

10. An electrode assembly adapted to apply stimulation signals to a neuromuscular pathway, the electrode assembly comprising a support structure having a first end and a second end, and an electrode mounted on the first end and a return electrode mounted on the second end, said support structure comprising a cylindrical tube having an outside diameter, the electrode being cylindrically shaped having an outside diameter and circumference equal to that of the support structure and being coaxial therewith, the electrode comprising a plurality of adjacent electrically conductive segments disposed around and forming such first end, a portion of each segment being coincident with said circumference, each segment being electrically isolated from every other segment, each segment adapted for contact with a selected neuromuscular pathway, each segment configured for coupling to a source of stimulation signals so that stimulation signals are deliverable to a selected neuromuscular pathway through one or more of the segments and the return electrode.

* * * * *